United States Patent
Chen et al.

(10) Patent No.: US 9,511,241 B2
(45) Date of Patent: Dec. 6, 2016

(54) IRRADIATION PLANNING FOR PARTICLE THERAPY

(71) Applicants: Wenjing Chen, Erlangen (DE);
Alexander Gemmel, Erlangen (DE);
Eike Rietzel, Weiterstadt (DE)

(72) Inventors: Wenjing Chen, Erlangen (DE);
Alexander Gemmel, Erlangen (DE);
Eike Rietzel, Weiterstadt (DE)

(73) Assignee: Siemens Aktiengesellschaft, München (DE)

( * ) Notice: Subject to any disclaimer, the term of this patent is extended or adjusted under 35 U.S.C. 154(b) by 201 days.

(21) Appl. No.: 13/708,438

(22) Filed: Dec. 7, 2012

(65) Prior Publication Data

US 2013/0150647 A1 Jun. 13, 2013

(30) Foreign Application Priority Data

Dec. 9, 2011 (DE) .................. 10 2011 088 160

(51) Int. Cl.
*A61N 5/10* (2006.01)

(52) U.S. Cl.
CPC ............. *A61N 5/103* (2013.01); *A61N 5/1031* (2013.01); *A61N 5/1038* (2013.01); *A61N 2005/1034* (2013.01); *A61N 2005/1041* (2013.01)

(58) Field of Classification Search
CPC .... A61N 5/103; A61N 5/1031; A61N 5/1038; A61N 2005/1034; A61N 2005/1041
USPC .......................................................... 600/1–8
See application file for complete search history.

(56) References Cited

U.S. PATENT DOCUMENTS

| 7,268,358 B2 | 9/2007 | Ma et al. |
| 7,920,675 B2 | 4/2011 | Lomax et al. |
| 2010/0327188 A1* | 12/2010 | Bert et al. .................. 250/492.3 |
| 2011/0272600 A1* | 11/2011 | Bert et al. .................. 250/492.1 |
| 2011/0303858 A1 | 12/2011 | Bert et al. |

FOREIGN PATENT DOCUMENTS

| DE | 10 2007 045 879 A1 | 4/2009 |
| DE | 10 2008 009 765 A1 | 9/2009 |
| DE | 10 2008 051 476 A1 | 4/2010 |
| EP | 2 108 402 A1 | 10/2009 |

OTHER PUBLICATIONS

German Office Action dated Dec. 3, 2012 for corresponding German Patent Application No. DE 10 2011 088 160.3 with English translation.

(Continued)

*Primary Examiner* — Samuel Gilbert
(74) *Attorney, Agent, or Firm* — Lempia Summerfield Katz LLC

(57) ABSTRACT

A method for producing an irradiation plan for a target volume includes preparing a modulation curve that characterizes modulation of particle numbers at target points in the target volume that lie one behind another in a direction of the beam. The method also includes determining a current position of the target volume and defining a plurality of target points that fully cover the target volume in the current position. Particle numbers are assigned to the plurality of current target points using the modulation curve.

11 Claims, 13 Drawing Sheets

(56) References Cited

OTHER PUBLICATIONS

Krämer M. et al., "Treatment Planning for Heavy-Ion Radiotherapy: Physical Beam Model and Dose Optimization," Physics in Medicine and Biology, vol. 45, pp. 3299-3317, 2000.
Lomax A., "Intensity Modulation Methods for Proton Radiotherapy," Physics in Medicine and Biology, vol. 44, pp. 185-205, 1999.
Rietzel E., et al., "Respiratory Motion Management in Particle Therapy," Med. Phys., vol. 37, No. 2, pp. 449-460, 2010.
European Search Report dated Aug. 20, 2013 for corresponding EP 2011P27497EP with English translation.

* cited by examiner

FIG 3

| | | | | |
|---|---|---|---|---|
| 1 | | ● | ● | |
| 2 | ● | ● | ⊘ | ○ |
| 3 | | ● | ● | |
| 4 | ● | ● | ⊘ | ○ |
| 5 | ● | ● | ⊘ | ○ |
| 6 | ● | ● | ⊘ | ○ |
| 7 | | ● | ● | |
| 8 | ● | ● | ⊘ | ○ |
| 9 | | ● | ● | |

FIG 4

| | | | | |
|---|---|---|---|---|
| 1 | ● | ● | | |
| 2 | ● | ● | ⊘ | ○ |
| 3 | ● | ● | | |
| 4 | ● | ● | ⊘ | ○ |
| 5 | ● | ● | ⊘ | ○ |
| 6 | ● | ● | ⊘ | ○ |
| 7 | ● | ● | | |
| 8 | ● | ● | ⊘ | ○ |
| 9 | ● | ● | | |

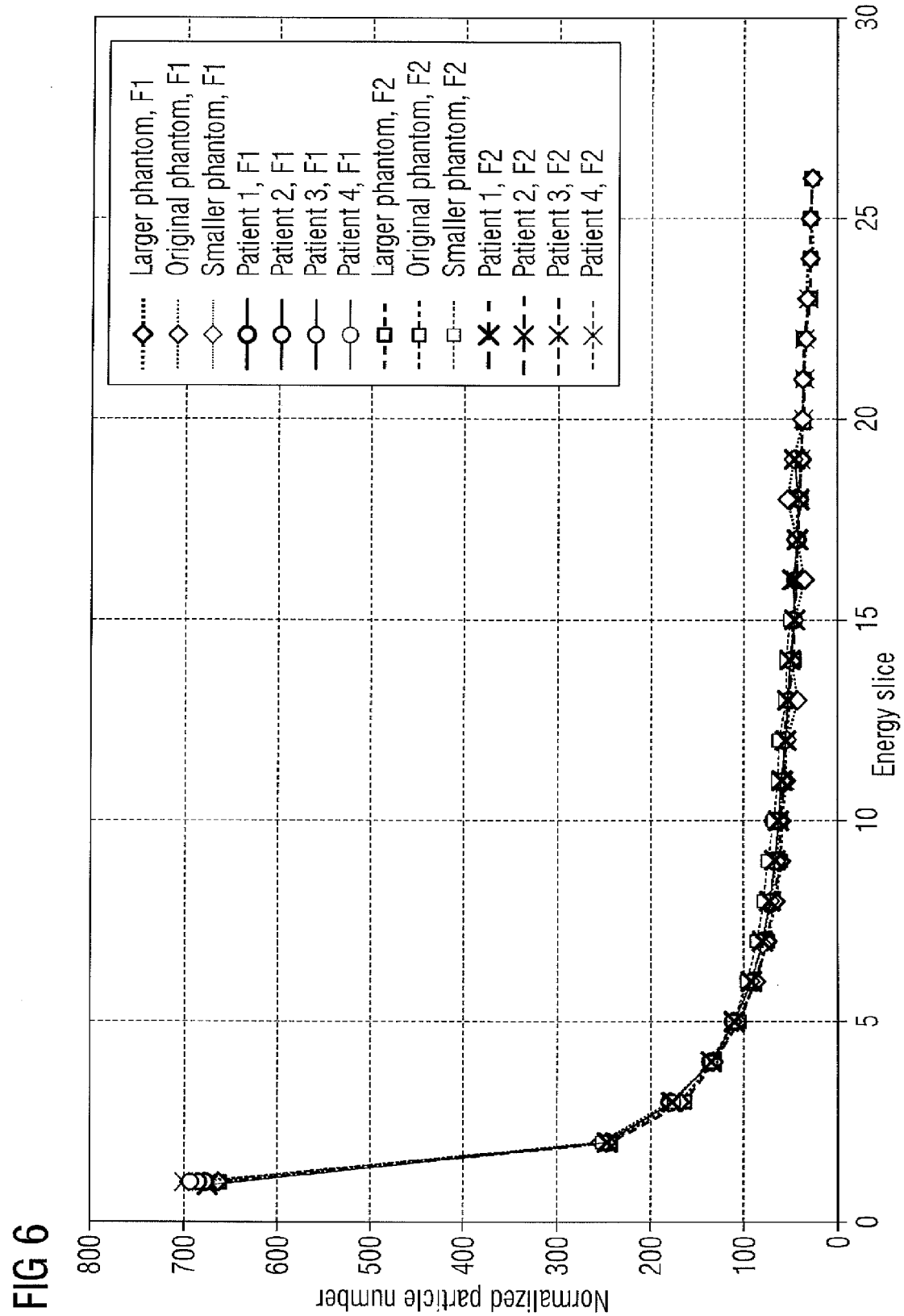

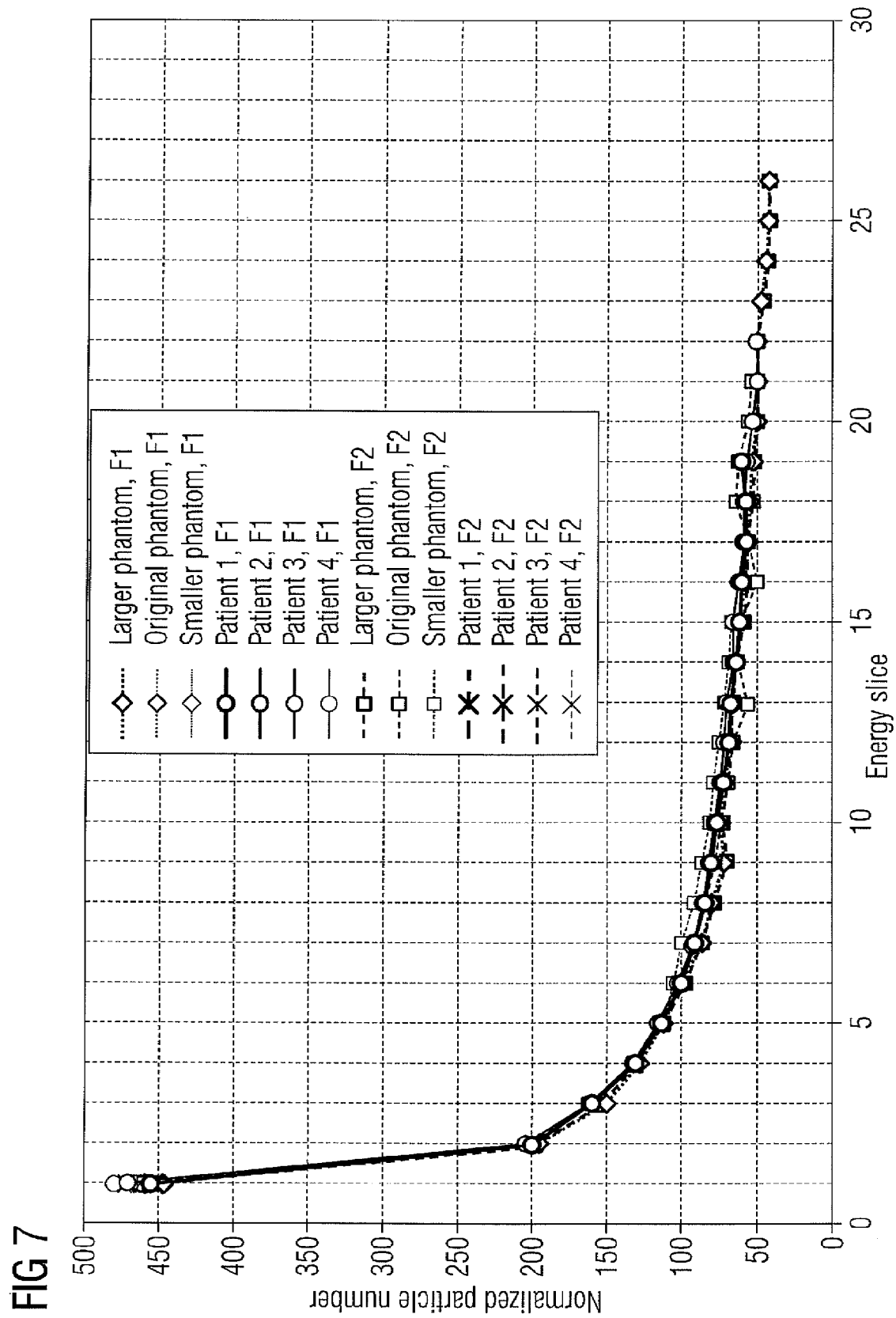

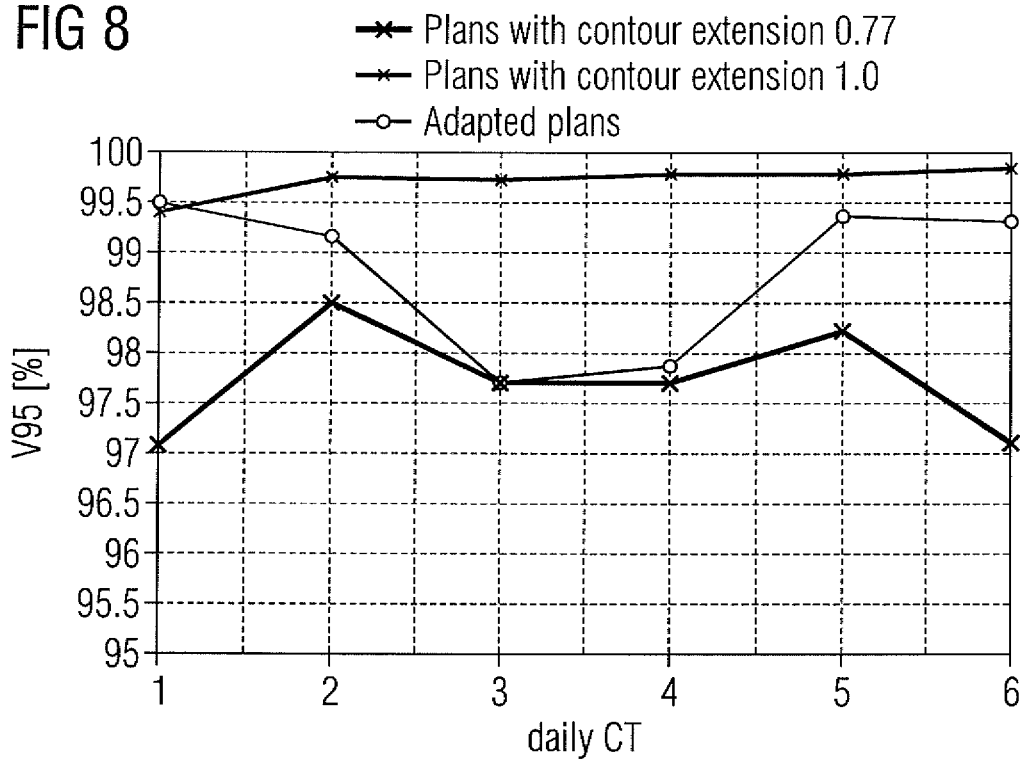
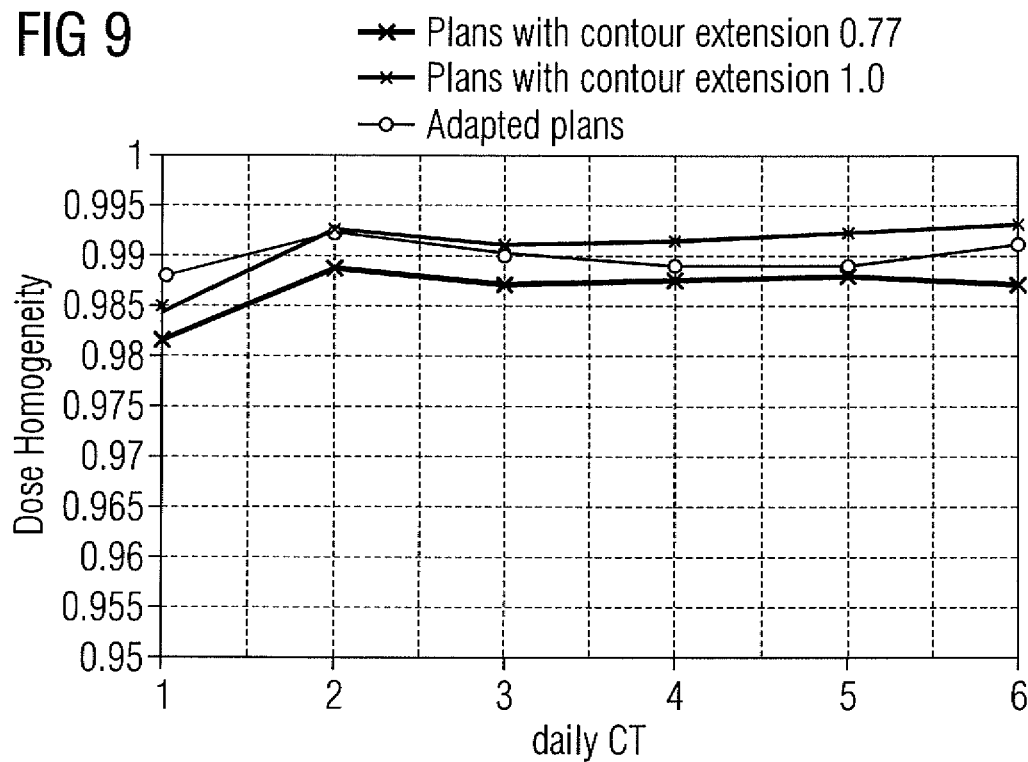

IRRADIATION PLANNING FOR PARTICLE THERAPY

This application claims the benefit of DE 10 2011 088 160.3, filed on Dec. 9, 2011, which is hereby incorporated by reference.

BACKGROUND

The present embodiments relate to a method for irradiation planning for particle therapy of a target volume.

As a preliminary to any particle therapy treatment, an irradiation plan is determined. Essentially, the irradiation plan defines how the target volume is to be irradiated in order to apply the desired dosage distribution in the body. In the case of particle therapy, the number of particles to be applied may be determined for each target point or grid point in the target volume.

For this purpose, an iterative optimization method may be used for the irradiation planning. Owing to the complexity of the calculation, the iterative optimization method may sometimes take a long time and necessitate a large computational effort to determine an irradiation plan such that a particular desired dosage prescription is satisfied in terms of irradiation of the target volume and the surrounding organs.

In addition, this determination of a suitable irradiation plan is made more complicated by the fact that the internal anatomy of a patient may change over time. For example, target volumes within the abdomen may change position from day-to-day or over the course of several days or weeks. A typical organ that may be subject to a change of position is the prostate gland. Thus, the bladder that lies beside the prostate gland and the rectum that lies close to the prostate gland may have an effect on the position and the shape of the prostate gland, depending on the extent to which the bladder and/or the rectum are filled.

Hence, an irradiation plan that is calculated one day may no longer be optimal for irradiating the patient on another day.

SUMMARY AND DESCRIPTION

The present embodiments may obviate one or more of the drawbacks or limitations in the related art. For example, a method of irradiation planning that enables rapid irradiation planning and precise adaptation of the irradiation plan to the target volume is provided.

The method for producing an irradiation plan for a target volume includes preparing a modulation curve that characterizes the modulation of particle numbers at target points in the target volume that lie one behind another in the direction of the beam (e.g., the beam direction). The current position of the target volume is determined. A plurality of current target points that fully cover the target volume in the current position is defined. Particle numbers are assigned to the current target points using the modulation curve.

An iterative optimization method that may be used for irradiation planning takes a long time and is computationally demanding.

Instead of this, for the purpose of achieving a prescribed planning objective, the irradiation planning is carried out with the assistance of a modulation curve.

In the case of an irradiation plan that has already been produced, the modulation of the particle numbers for target points that lie one behind another only has a small variation through the entire target volume. The directional specification "one behind another" refers to the beam direction. Target points that lie one behind another are thus arranged one behind another in the direction of the particle beam. Target points that lie one behind another may be assigned to different energy slices. A target point that lies at a more distal position thus has a higher energy level than a target point that lies at a more proximal position.

The modulation of the particle numbers looking in the beam direction is also comparatively similar for irradiation plans calculated from different CT datasets for the same patient. The modulation is also comparable between different patients.

Based on this analysis, for the purpose of irradiation planning, it is no longer necessary to use the time-consuming optimization method. Rather, the irradiation planning may be carried out with the aid of a modulation curve.

This modulation curve describes how the particle numbers in an irradiation plan for the target volume to be irradiated change within the target volume when looking in the beam direction. In the vast majority of cases, the modulation curve describes the decrease in the numbers of particles from the distal to the proximal. The modulation curve may be implemented, for example, by an analytical function or also by a one-dimensional array, from which the particle numbers change may be read off for target points that lie one behind another.

Since the modulation curve relates to the modulation of the particle numbers in the beam direction, the modulation curve may also be referred to as a depth modulation curve (DMC).

One aspect is the extraction of the modulation curve or the depth modulation curve from the particle numbers for a plan that already exists (e.g., from several existing plans). This modulation curve may be used as the basis for the determination of a new plan or, more precisely, for the determination of the particle numbers in a new plan.

By comparison with a conventional optimization, based on an iterative optimization of an objective function in order to achieve a prescribed dosage in terms of a desired distribution of the dose, the proposed method does represent only an approximation method, but in many cases, it supplies adequately good results. With the help of this approximation method, a plan may be rapidly adapted.

An adaptation of an existing irradiation plan (re-planning) may be completed very rapidly (e.g., within 1 min) if the current position of the target volume (e.g., the current contour of the target volume) is available. The proposed method for adapting a plan may be carried out both online during adaptation of the beam (e.g., during a irradiation fraction or even during the application of the beam) or during offline re-planning. In one embodiment, the method is used for planning in the case of a new patient, for whom no irradiation planning has yet been carried out.

The target points that fully cover the target volume, for which particle numbers have then been determined and assigned, may, for example, be irradiated in a scanning procedure, in that a particle beam is directed in succession at one target point after another until the assigned number of particles has been applied to the target point concerned. The scanning procedure used may be, for example, a raster (grid) scanning method, in which the particle beam scans from grid point to grid point. The target points may also be referred to as grid points. However, other scanning procedures such as, for example, continuous scanning may be used. In addition, different variants of scanning such as, for example, rescanning, in which the grid points are targeted several times for the purpose of applying the dose, may be used.

The modulation curve may be determined in a preliminary procedure from at least one existing irradiation plan, in which an assignment of particle numbers to target points in the target volume is stored.

The existing irradiation plan may, for example, have the same irradiation objective (e.g., the same prescription in terms of dosage for the target volume, dosage for the organs at risk) as for the irradiation plan that is to be determined by the method of the present embodiments. If several existing irradiation plans are being used, a modulation curve may, for example, be determined from each irradiation plan, and, if necessary after normalization, the modulation curves may be averaged.

In one embodiment, the target volume that is used in the preliminary procedure for determining the modulation curve may belong to the same person as the target volume, for which the current position is being determined. In this way, if re-planning takes place for the same patient, an existing irradiation plan may, for example, be used, and the existing irradiation plan may be modified for any change in position and/or shape that has occurred.

The target volume that is used in the preliminary procedure for the determination of the modulation curve may belong to a different person from the target volume, for which the current position is being determined. For example, an existing irradiation plan that has been produced for the target volume may be used in one person in order to determine a modulation curve that is used in the method of the present embodiments for the production of an irradiation plan for the same target volume in another person.

In one embodiment, the target volume that is used in the preliminary procedure for the determination of the modulation curve belongs to a phantom that models the target volume. Even an irradiation plan for a target volume modeled in a phantom may be sufficient in itself to determine a modulation curve that is then used in producing irradiation plans for humans.

The modulation curve may be determined in the preliminary procedure by averaging the particle numbers for several target point lines. A target point line is defined by target points that lie one behind another in the beam direction. A target point line defines the path of a narrow beam through the target volume or the target points that the narrow beam hits on its way. This may be a row of target points that lie one behind another in the direction of radiation.

For each target point line of the several target point lines, the decrease in the particle numbers from distal to proximal positions may be determined. Following this, the particle number modulations assigned to the various target point lines may be averaged, and from this, the modulation curve may be produced.

The modulation curve may be normalized with respect to the energy level of the particle beam required for irradiation of the target volume. Normalization provides, in effect, that the particle numbers are multiplied by a factor. The normalization may be effected, for example, in that the particle numbers are divided by the energy level of the most distal energy slice. Such normalization is particularly helpful when the modulation curve is to be used for the determination of particle numbers for a target volume that, for the purpose of irradiation, requires a particle beam with a different energy level from the reference target volume (e.g., when the range of the particle beam requires adaptation for the purpose of the irradiation). For example, the irradiation plan, from which the modulation curve is determined, may use a different range (e.g., a different maximum) for the particle beam than does the target volume having the current position the irradiation plan is being determined with the aid of the modulation curve.

Inaccuracies that would arise due to the transfer of the particle numbers from an existing plan to a new plan if there is an excessive difference in the range of the particle beam between the new and the existing plan are compensated by the normalization. When the particle numbers are transferred from an existing to a new plan, the particle numbers may in entirety be multiplied by a factor that corresponds to the quotient of the maximum energy of the particle beam for the new plan and the maximum energy of the particle beam for the old plan.

In one embodiment of the method, the current position of the target volume is determined by effecting the registration of a current three-dimensional image dataset (e.g., a CT dataset) against an earlier three-dimensional dataset (e.g., a planning CT), where the shape and/or the position of the target volume in the earlier dataset is known. The shape and/or the position of the target volume from the earlier dataset may thus be transferred across to the current dataset. For example, a contour of the target volume may be transferred across from one dataset to another dataset in order to identify the current shape and/or position of the target volume.

In determining the plurality of target points that fully cover the target volume in the current position, the target point spacing (e.g., in the beam direction or in a direction perpendicular to the beam direction) may be selected to correspond to a reference plan that already exists.

For example, the target point spacing may be adopted from the reference plan, from which the modulation curve was determined. In this way, it is easy to transfer across the particle numbers from the modulation curve onto the current target points. For example, it is thereby possible to avoid any interpolation of the array elements that describe the modulation curve.

In one form of embodiment of the method, when assigning particle numbers to the current target points on a target point line that is formed from current target points, the particle numbers that are specified by the modulation curve may be assigned.

Particle numbers that are specified by the modulation curve and are assigned to the current target points may, before the particle numbers are assigned to a target point line including current target points, be adjusted with respect to the energy level that is required for irradiation of the target volume. In this way, the method may compensate for penetration depths that differ compared to the reference target volume because of a change in the position and/or shape of the current target volume.

The method may be used for the calculation of an irradiation plan with optimized physical or biological distribution of the dose.

The proposed method is advantageous, for example, for an irradiation plan with a biologically optimized dosage distribution because, compared to conventional optimization using an objective function that is to be iteratively optimized, it permits an especially large time saving.

The method may be used for transferring an irradiation plan that already exists across to a new irradiation plan. The existing irradiation plan and the new irradiation plan may be assigned to the same patient. However, the existing irradiation plan and the new irradiation plan may be assigned to different patients. The existing irradiation plan may be assigned to a phantom, and the new irradiation plan may be assigned to a patient.

In one embodiment, the method may be carried out for the determination of particle numbers in the case of a irradiation field where the modulation curve is determined not from the first irradiation field but from a second or third irradiation field, for which the radiation has a different angle of incidence compared to the first irradiation field.

This great flexibility of the method is possible because modulation curves are very similar, even between different persons, between phantoms and persons and across different irradiation fields.

In one embodiment of the method, several modulation curves that, for example, may be stored in a database may be prepared. These modulation curves may be generated from different irradiation plans that differ in terms of the target organ, dosage objective, type of particle to be used and/or target point spacing. In assigning particle numbers to the current target points, one of the modulation curves may be selected (e.g., the modulation curve, for which the requirements of the original irradiation plan best correspond with the requirements of the new irradiation plan).

The irradiation planning apparatus of the present embodiments has a computing device and includes a component for preparing a modulation curve that characterizes the modulation of particle numbers at target points that, in the beam direction, lie one behind another in the target volume. The irradiation planning apparatus also includes a component for determining the current position of the target volume, a component for defining a plurality of current target points that fully cover the target volume in the current position, and a component for assigning particle numbers to the current target points, making use of the modulation curve. The computing device may include one or more processors and memories for storing instructions for configuring the processors.

The computing device may, for example, be constructed such that an embodiment of the method as described above is implemented.

The preceding and the following description of the individual features, their advantages and their effects refers both to the nature of the device and also to the nature of the method without this being explicitly mentioned in detail in every case. The individual features thereby disclosed may also be provided in combinations other than those indicated.

BRIEF DESCRIPTION OF THE DRAWINGS

FIG. 3 and FIG. 4 show a schematic diagram of exemplary grid points and iso-energy slices to explain the acts in the method;

FIG. 6 and FIG. 7 show exemplary normalized modulation curves for different physical or biological irradiation plans;

FIG. 8 to FIG. 11 show exemplary results of an analysis of the quality of the method in the case of an intra-patient adaptation;

DETAILED DESCRIPTION OF THE DRAWINGS

An exemplary sequence of activities in the method is shown with reference to FIG. 1 to FIG. 4.

Figure 1:
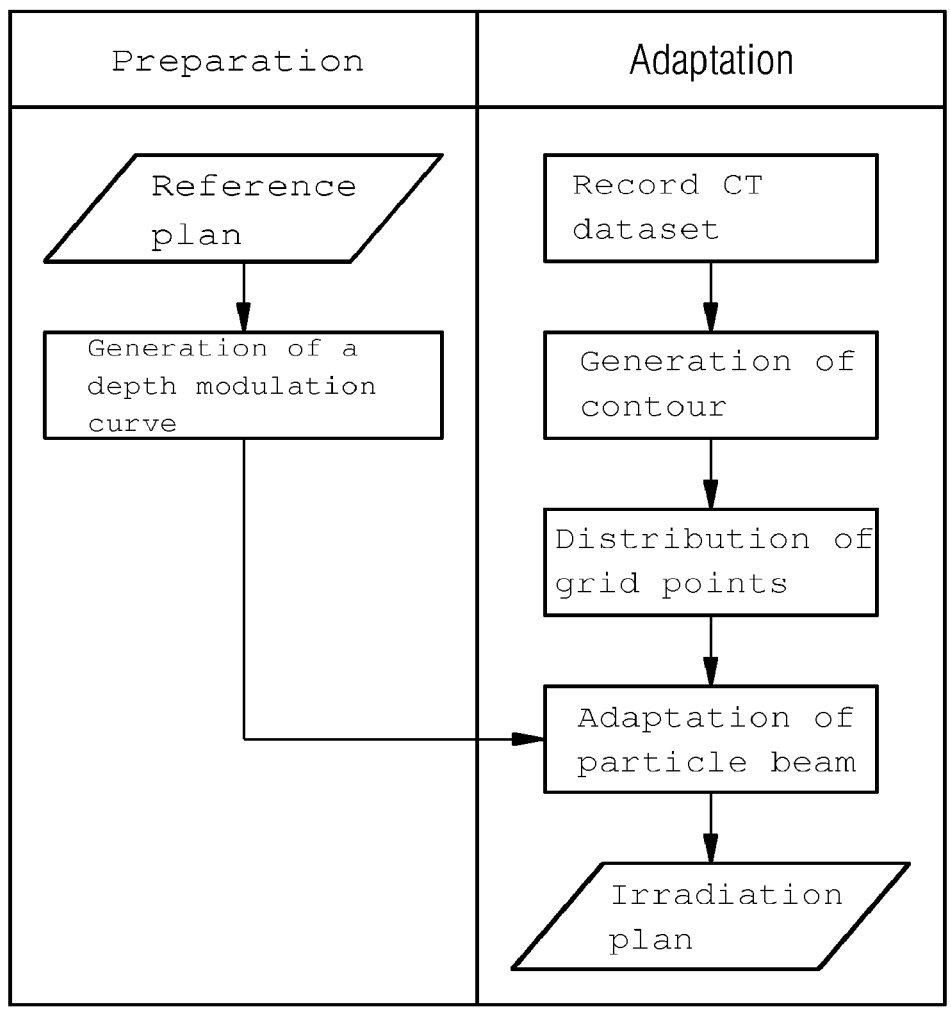
FIG. 1 shows a flow diagram for an embodiment of a method for calculating an irradiation plan from a particle number graph.

FIG. 1 shows the method acts for an exemplary sequence of activities in the adaptation procedure.

As preparation for the method, a particle number graph is generated. The particle number graph specifies modulation of particle numbers at different depths in a target volume (e.g., a depth modulation curve (DMC)). The DMC is generated from one or more reference plans.

This may be, for example, an original patient plan (e.g., for online adaptation of the irradiation planning or for re-planning). This may also be the plan for a reference patient or a plan for a phantom. From this plan (or from several plans), a new irradiation plan may also be calculated for a new patient "from the ground up."

For the purpose of calculating a plan for a current patient's anatomy, a CT dataset is recorded. The target volume or a contour of the target volume, as applicable, is mapped in, for example, by a user or by a deformable transformation of a reference target volume that is already available. The iso-center of the target volume is defined.

Grid points are distributed over the new target volume, and from the modulation curve, particle numbers are produced for each grid point.

In this way, an irradiation plan that is adapted appropriately to the current patient's anatomy is obtained.

The method for producing the DMC, for distributing the grid points, and for adapting the particle numbers is explained in more detail below.

Generation of the DMC

Figure 2:
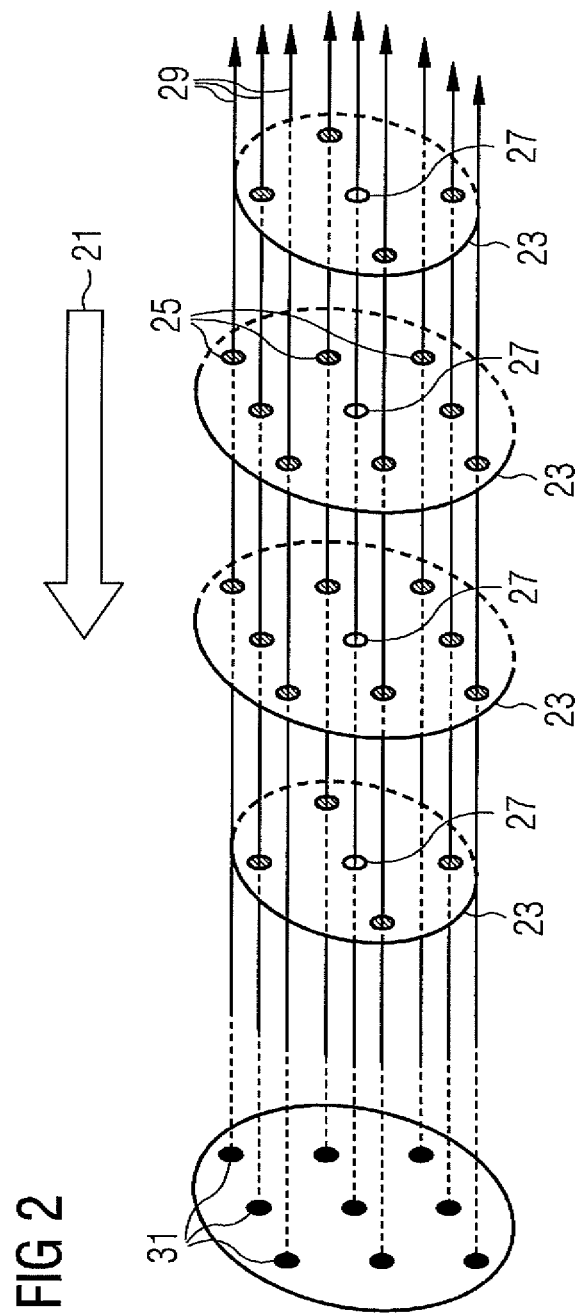
FIG. 2 shows a diagram of exemplary iso-energy slices, grid point slices and radiation lines.

For the purpose of illustration, FIG. 2 shows, in simplified and schematized form, an exemplary convex target volume made up of four iso-energy slices 23. The target volume is fully covered by a plurality of grid points 25.

The thick arrow 21 shows a direction of incidence of the particle beam. The distal slice is located on the left, and the proximal slice is located on the right. In each slice, the central grid point 27 represents the iso-center.

The grid points 25 may be projected along a beam line 29 (e.g., in the beam direction). In the case of the target volume shown in FIG. 2, the result of this is a total of nine beam lines 29 or nine grid point projections 33, as applicable.

Details for the irradiation of a target volume such as, for example, the grid point positions, the energy levels and the items of field data (e.g., the number of fields and the angle of incidence of the beam) may be taken from one or more reference plans. The one or more reference plans will have been produced and optimized in terms of the prescribed physical dose or RBE-weighted dose using a conventional irradiation planning method.

The modulation curve DMC is produced for each field in the one or more irradiation plans by carrying out the following acts.

In a first act, the grid points, on a plane in a reference plan perpendicular to the beam direction, are projected as illustrated in FIG. 2.

For each beam line that passes through grid points on the same grid point projection, the particle numbers are extracted for each energy slice along the beam line. These may be stored in a one-dimensional array or vector, with the grid point that lies farthest away distally as the starting point of the vector.

Figures 3, 4:
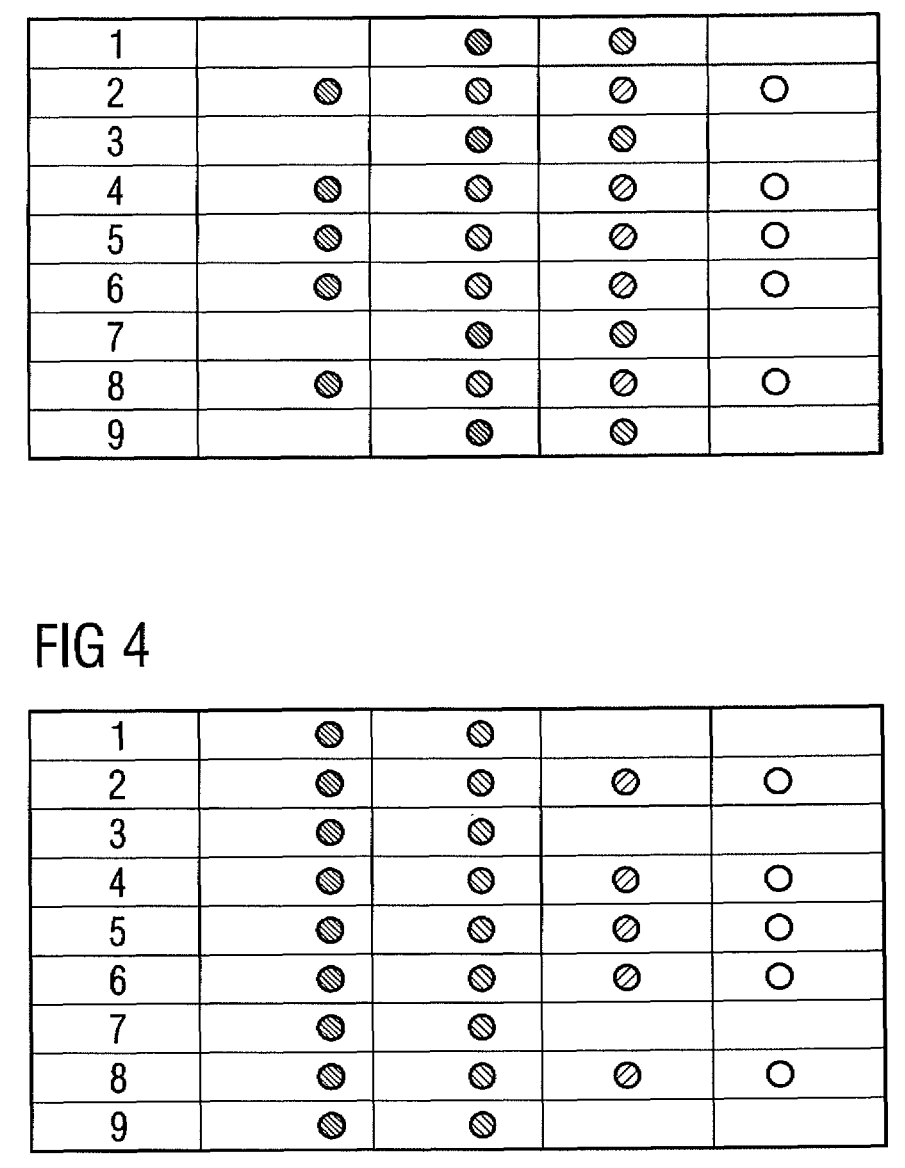

FIG. 3 shows in tabular form the grid points or particle number vectors, as applicable, belonging to the new beam lines. The left-hand column corresponds to the distal iso-energy slice, and the right-hand column belongs to the proximal iso-energy slice. The hatching density indicates qualitatively the particle numbers assigned to the grid points. The particle numbers may be seen to decrease in the distal to proximal direction.

All the particle number vectors are displaced in such a way that the starting values all begin at the energy slice of the distal edge.

FIG. 4 shows in tabular form the particle number vectors belonging to the new beam lines that have been displaced to the distal iso-energy slice. These vectors now begin at the most distal iso-energy slice (e.g., at the slice, at which the particle beam would exit from the target volume again).

The depth modulation curve may be calculated by calculating the mean value of the displaced particle number vectors. For example, the averaging is carried out over the columns in FIG. 4.

The particle numbers for the averaged vector (e.g., the particle numbers along the DMC) are divided by the energy level of the energy slice that lies furthest away distally. By this normalization, differences may be compensated for in terms of the position of the target volume in the patient/object that is to be irradiated.

If there are several reference plans, the normalized DMCs for each of these plans may be determined and then averaged.

Figure 5:
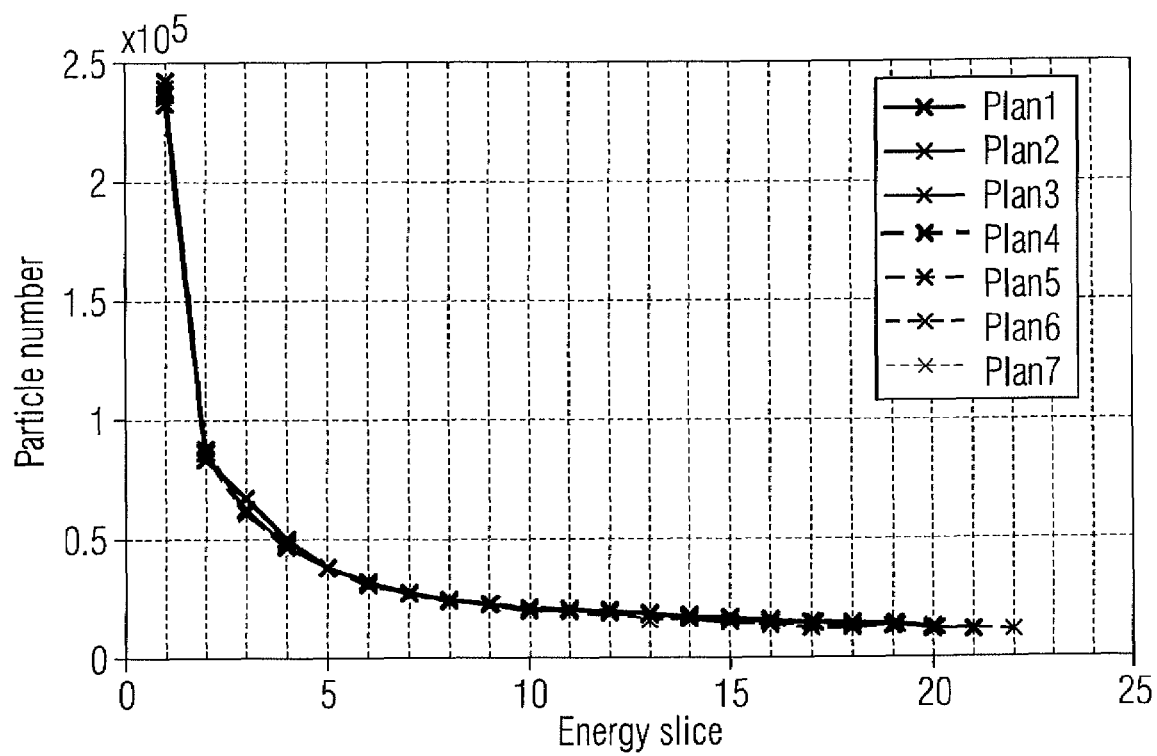
FIG. 5 shows exemplary unnormalized modulation curves that have been derived from physical treatment plans.

FIG. 5 shows the unnormalized DMCs (particle number vs. energy slice) that have been derived from physical treatment plans produced from different CT datasets for the same prostate-gland patient and relate to an irradiation field (F1). The dosage objective was a physical dose of 1 Gy at two fields lying opposite each other (+90° and −90°). The unnormalized DMCs are in very good agreement.

FIG. 6 shows normalized DMCs (e.g., normalized particle number vs. energy slice) for different irradiation plans belonging either to phantoms (e.g., larger phantom, original phantom, smaller phantom) or to different patients (e.g., patient 1 to patient 4) for different irradiation fields (e.g., F1 and F2). The irradiation plans are, for example, irradiation plans that have been optimized with respect to the physical dose.

FIG. 7 shows particle number graphs analogous to FIG. 6, except that the DMCs have been produced from irradiation plans that had been optimized with respect to the biological dose.

In the case of FIG. 6, underlying each of the physical irradiation plans is a fractional dose of 1 Gy. For each of the biological irradiation plans in FIG. 7, the underlying fractional dose is 3 Gy. The irradiation plans are optimized for each of two irradiation fields lying opposite each other.

The DMCs for the biological plans differ somewhat more from each other than the DMCs for the physical plans. However, all the DMCs still agree well with each other.

Determination of the Irradiation Fields and the Grid Points

A description of how the irradiation fields or grid points, as applicable, are determined, so that irradiation planning may be carried out on the basis of a new mapping dataset follows.

After a new CT dataset has been recorded, and the contour and the iso-center of the target volume have been determined, the gird points are distributed as described below.

The water-equivalent path length (WEPL) in the beam direction is calculated for each voxel in the CT dataset. For this purpose, the method described in M Krämer et al, "Treatment planning for heavy-ion irradiation: physical beam model and dose optimization," Phys. Med. Biol. 45, 2000, pp. 3299-3317, may be used (e.g., making use of the published equation (7)).

After this, the energy slices are defined for the adaptation of the plan, taking into consideration the WEPL of the target volume. For this purpose, the energy spacings used may be essentially the same as the energy spacings defined for the one or more reference plans.

A new grid with the iso-center of the target volume as the origin is created. The grid spacings may be chosen to be essentially the same as the grid spacings of the one or more reference plans.

Grid points are distributed over the new grid in order to cover fully the target volume with grid points on every energy slice. In doing this, use may be made of target volume contour extensions that are essentially similar to or the same as the target volume contour extensions that were also used in the one or more reference plans.

Adaptation of the Particle Numbers

The particle numbers may be determined for the new grid points by using the DMC previously generated.

The new grid points are projected perpendicular to the beam direction.

For each projected grid point, the particle numbers along the assigned beam line are determined for the grid points along this beam line. In doing this, the starting point is the energy slice, from which the beam exits from the target volume again. The series of grid points lying before the start point are now assigned the particle numbers from the DMC. Before doing so, the normalized DMC is first multiplied by the energy level of the most distal energy slice that occurs in the new plan. In this way, the normalization that had previously been carried out is reversed, and differences, in terms of the penetration depths required for the target volume, between the reference plan and the current plan are compensated.

If the number of iso-energy slices, through which the beam line passes, is larger than the length of the DMC, the last particle number from the DMC may be assigned to the projecting grid points. This is acceptable because the tail of a DMC is broadly flat.

Results

What follows is an investigation of irradiation plans adapted using the above method. On the basis of the similarity of the DMCs for different plans for the prostate patient examples and for the phantoms for both fields, the following analyses were performed, both for physically optimized and for biologically optimized plans: adaptation of a reference plan to a further CT dataset for the same patient (e.g., intra-patient adaptation); adaptation of a plan for a patient to another patient (e.g., inter-patient adaptation); adaptation of a phantom plan to a patient (e.g., phantom-patient adaptation); and adaptation of a DMC derived from a field to both fields of the adapted plan (e.g., inter-field adaptation).

Intra-Patient Adaptation

The intra-patient adaptation was tested for physical irradiation plans using the example of a prostate gland patient.

For example, a CT dataset was selected at random from a series of CT datasets for the patient, as the reference dataset.

The DMC was determined from the assigned physical irradiation reference plan. Using the method described above, adapted irradiation plans were generated for the remaining CT datasets.

In the case of the intra-patient adaptation, normalization of the DMC, by dividing by the most distal energy level, was forgone because when the patient is the same, any differences in range in the beam direction are so small that their effect on the particle numbers is negligibly small.

Figure 10:
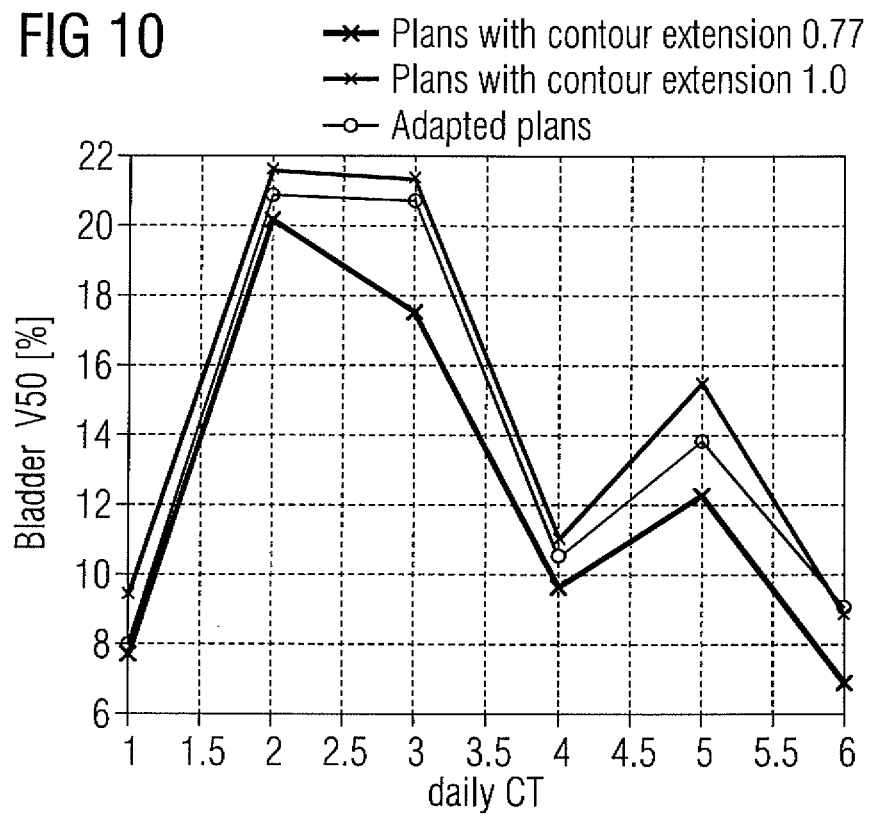
Figure 11:
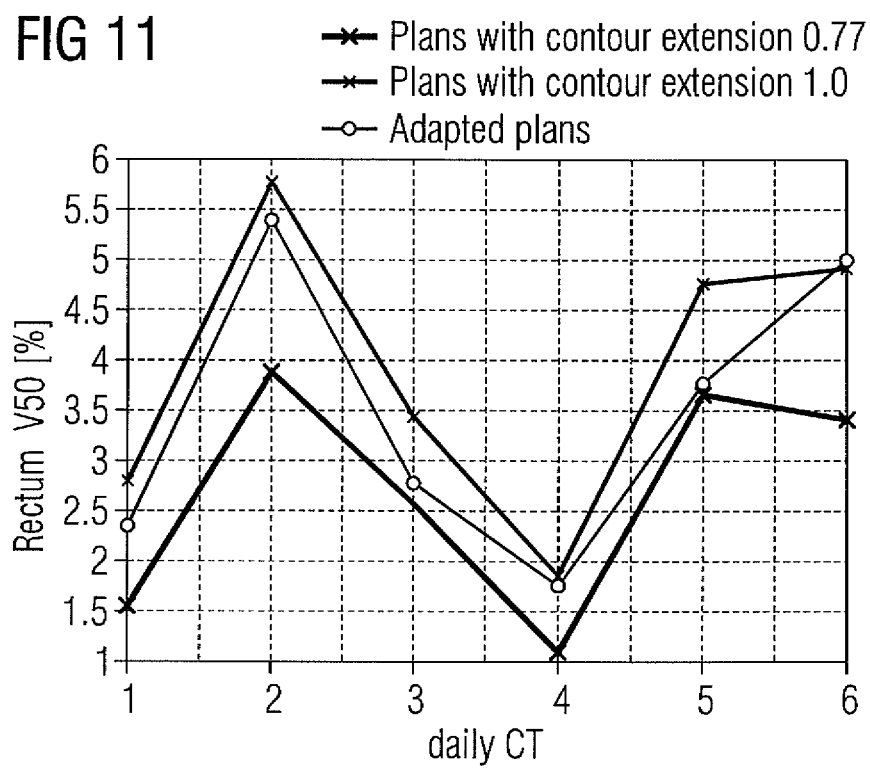
Figure 12:
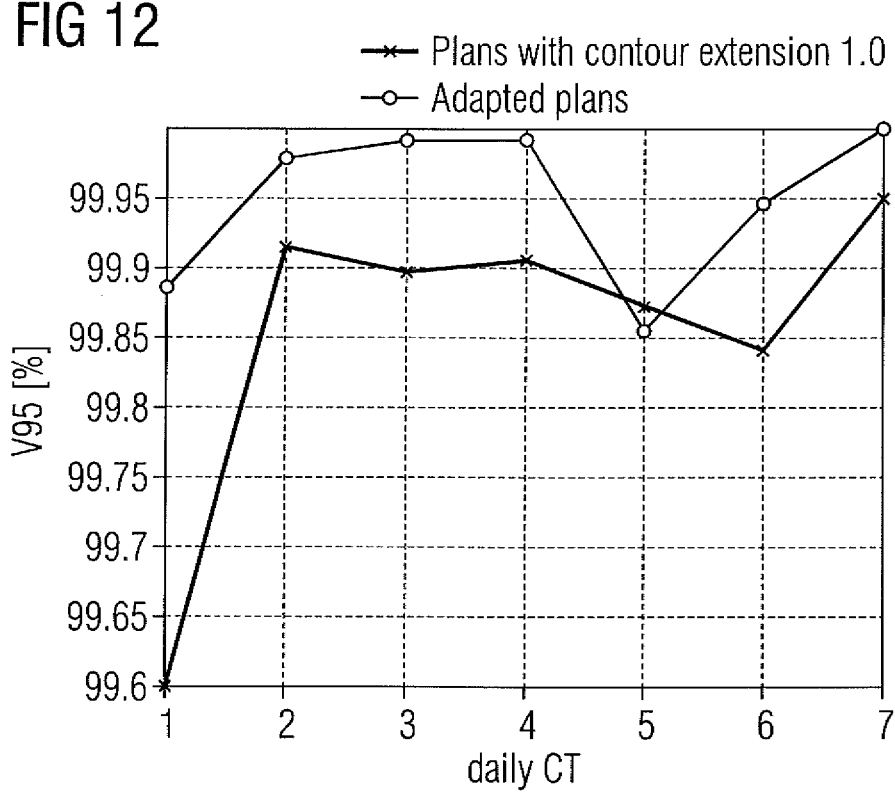
FIG. 12 to FIG. 15 show exemplary results of an analysis of the quality of the method in the case of an inter-patient adaptation.
Figure 13:
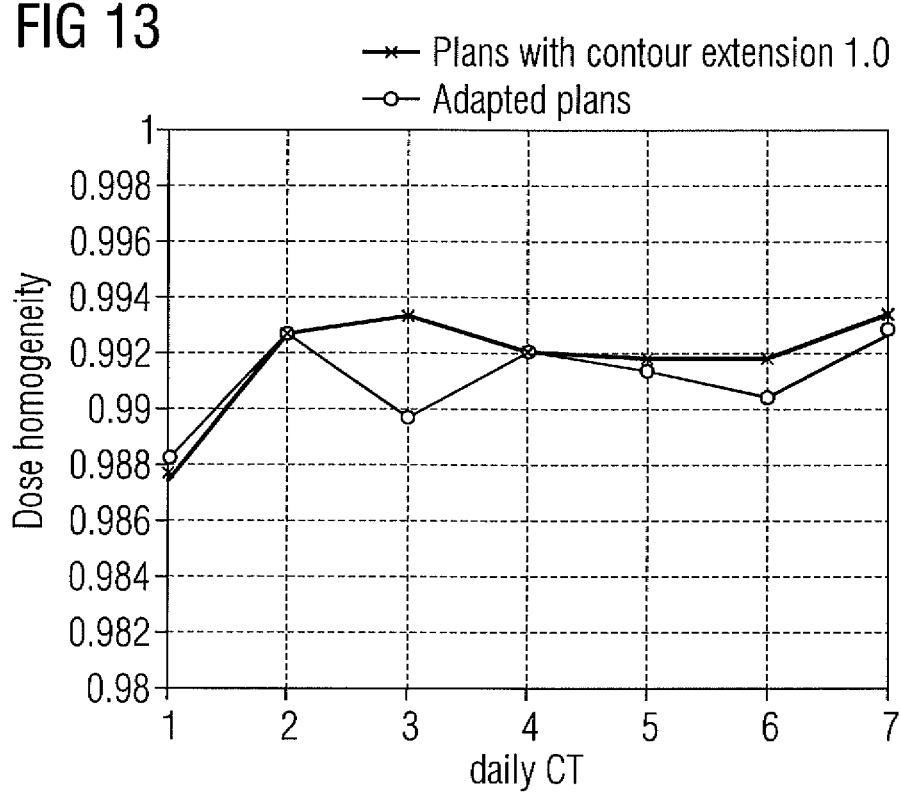
Figure 14:
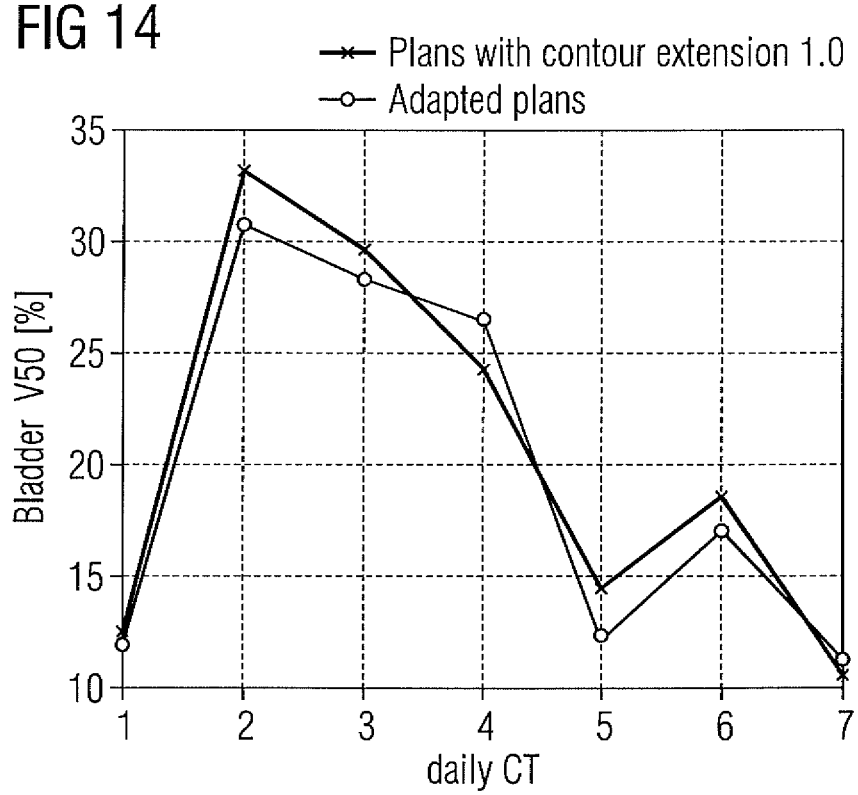
Figure 15:
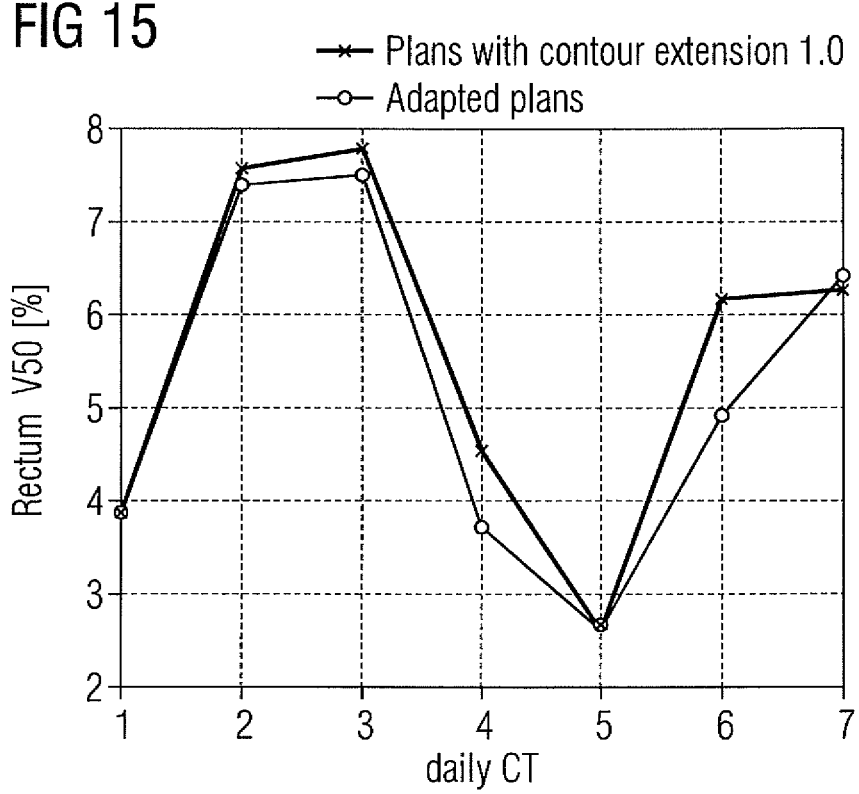

The V95 for the target volume (FIG. 8), the dose homogeneity within the target volume (FIG. 9), and the V50 for organs at risk (e.g., in the case of the prostate gland, the bladder and the rectum; FIG. 10 and FIG. 11) were calculated for the adapted plans that are applied to the relevant CT datasets, and were compared with the corresponding variables of the plans that had been calculated for the CT datasets concerned using conventional methods.

In FIG. 8 to FIG. 11, plans for different CT datasets (e.g., daily CTs) that were calculated using conventional optimization (e.g., for irradiation plans with contour extensions of 0.77 and 1.0) are compared with the plans adapted in accordance with the method disclosed.

A satisfactory dosage cover and homogeneity for the target volume together with a comparable dosage load for the organs at risk may be achieved.

Inter-Patient Adaptation

Inter-patient adaptation was tested in an analogous way as for the intra-patient adaptation, by reference to biological plans.

For this purpose, biological plans for a typical patient (e.g., patient 2) were adapted for different CT datasets in accordance with the procedural sequence explained above, in that the DMC used was the DMC determined from a plan for another typical patient (e.g., patient 3).

As shown in FIG. 12 to FIG. 15, the dosage cover, the homogeneity and the load on the organs at risk are satisfactory.

Phantom-Patient Adaptation and Inter-Field Adaptation

Both of these plan adaptations were again tested by reference to biological plans.

Figure 16:
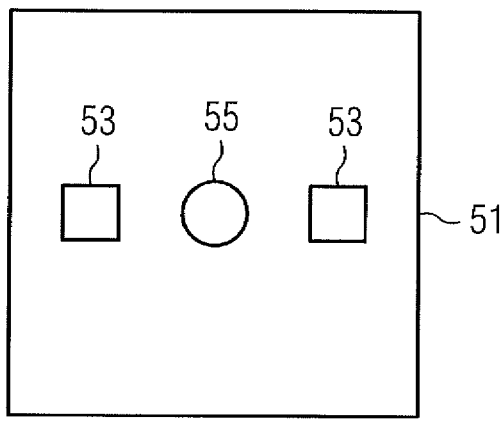
FIG. 16 to FIG. 18 show exemplary datasets from different phantoms for a prostate gland irradiation.
Figure 17:
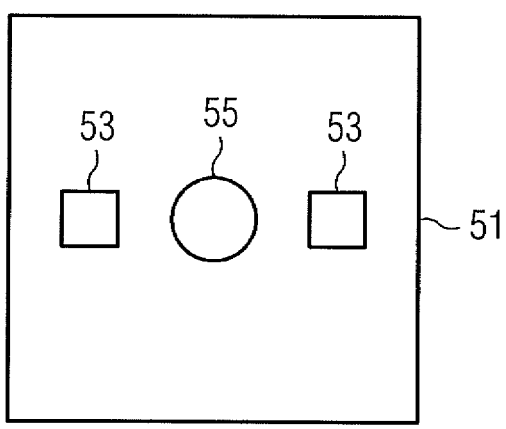
Figure 18:
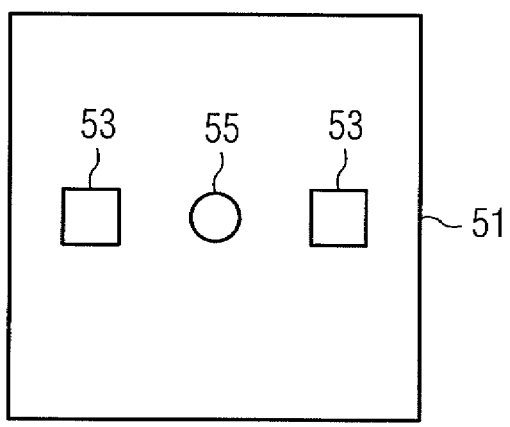
Figure 19:
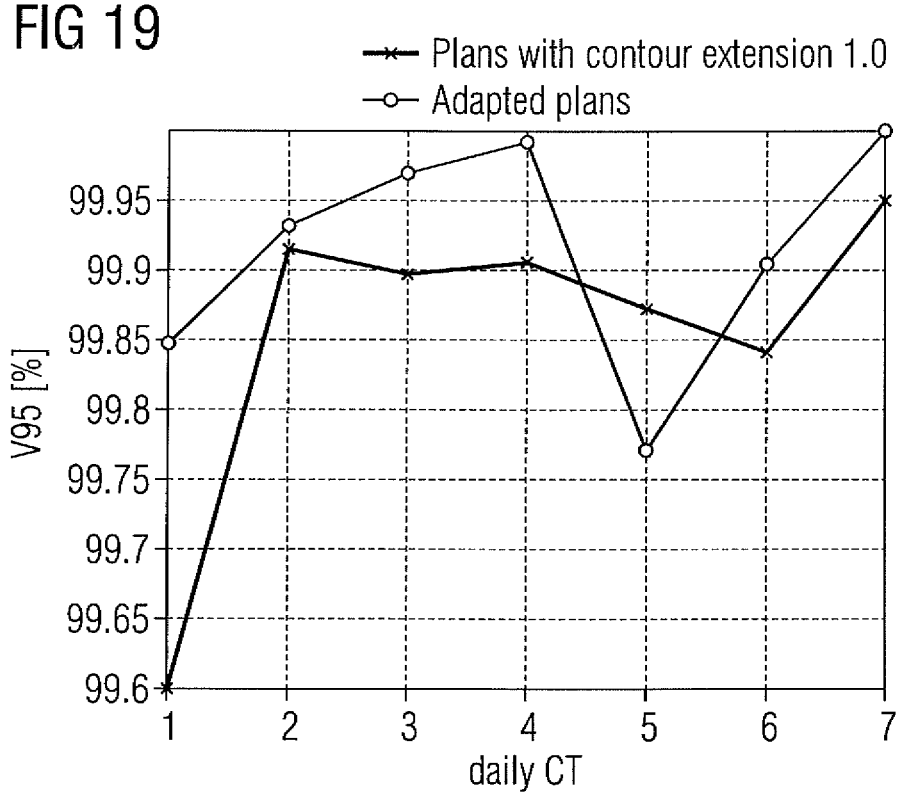
FIG. 19 to FIG. 22 show results of an analysis of the quality of the method in the case of a phantom-patient adaptation and interfield adaptation.
Figure 20:
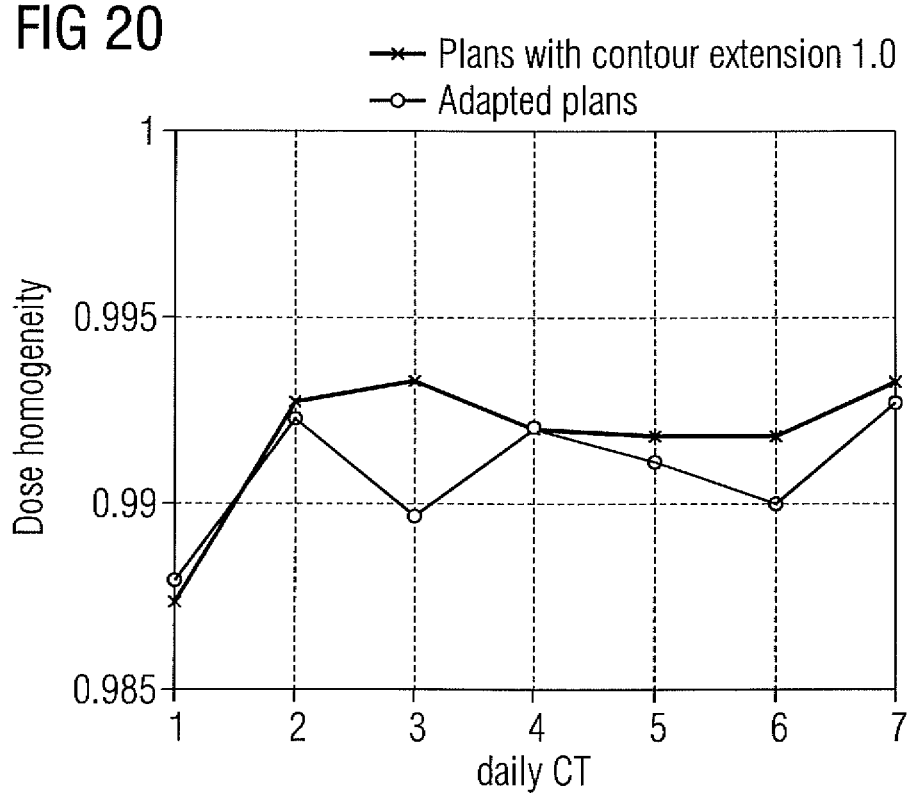
Figure 21:
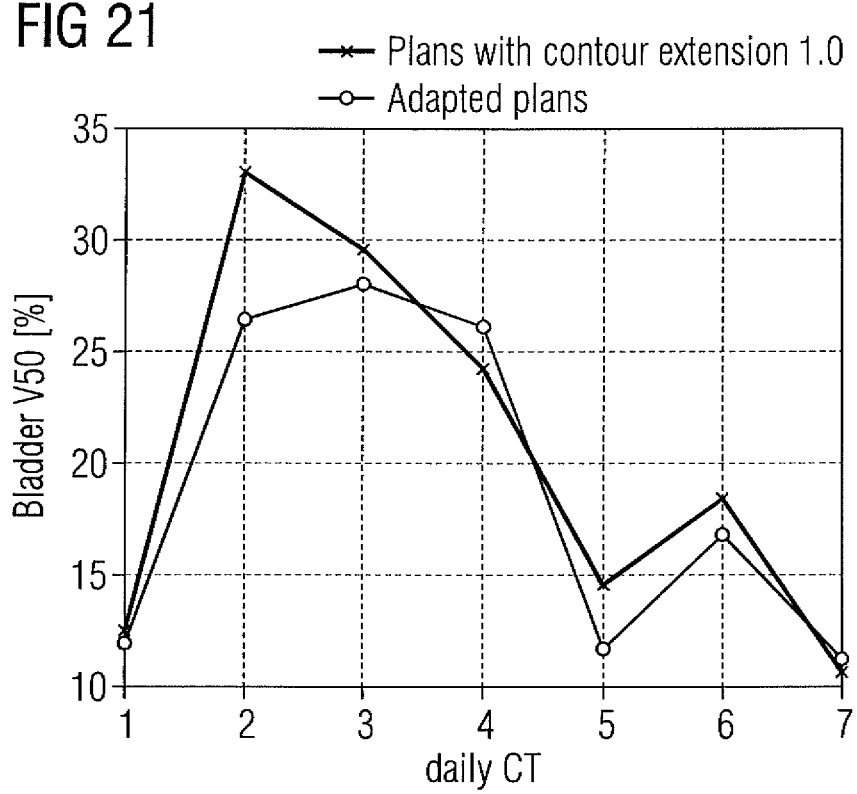
Figure 22:
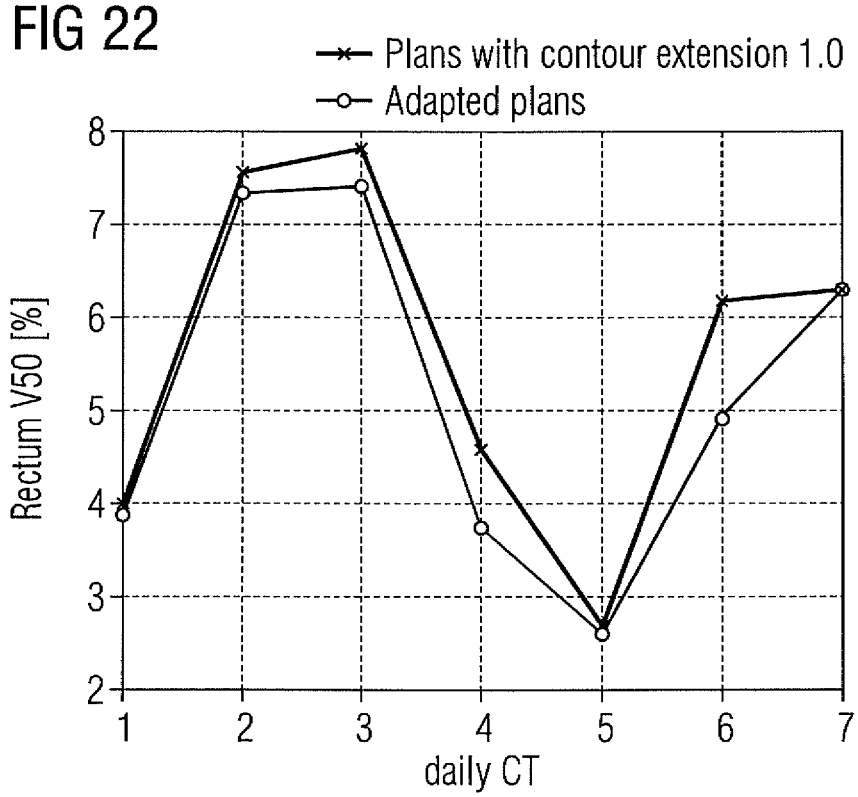

For phantom-patient adaptation, three prostate gland carcinoma phantoms with different target volumes, or their virtual CT datasets, were generated with the aid of MATLAB. FIG. 16 to FIG. 18 show the structure of the phantom with a body 51, bony structure 53 and a target volume 55. The different sizes of the target are shown.

An average DMC was calculated. The basis of the averaging is the normalized DMCs of the biological plans for the three phantoms. By reference to this average DMC, the patient plan was adapted to the different CT datasets. In doing this, the DMC for one field (e.g., the +90° field) was adapted for both fields in the new plan in order to test the inter-field adaptation.

FIG. 19 to FIG. 22 show the results of the analysis, analogously to FIG. 8 to FIG. 11 or FIG. 12 to FIG. 15.

The dosage cover, homogeneity and the loading on the organs at risk are satisfactory by comparison with the conventionally-calculated plans for the CT datasets.

Limits of the Method and Solution

The method is suitable for convex target volumes with consecutive target points along the beam direction. Otherwise, the situation may arise that the dosage distribution and the protection of organs at risk are detrimentally affected.

In one embodiment, in such cases, field patching, in which a concave target volume is subdivided into several convex parts to get round the problem of a concave target volume when adapting the plan, may be carried out.

The method for planning or re-planning on the basis of a DMC, for the purpose of determining the particle numbers for grid points, permits a plan to be calculated very rapidly compared to the time-consuming dosage optimization (e.g., for biological plans).

In the test with phantom datasets and datasets for different prostate gland patients, excellent coverage of the target volume and dose homogeneity may be achieved, at the same time as a similar dose loading on organs at risk, for intra-patient adaptation, for inter-patient adaptation, for phantom-patient adaptation and also in the case of inter-field adaptation.

The comparison refers to a comparison of plans that have been determined using the method of the present embodiments against plans calculated in accordance with a conventional method.

Plan calculation may be carried out very rapidly (e.g., in less than one minute in the case of an implementation making use of the commercially available MATLAB) and thus has the potential for being used even for online adaptation to compensate for inter-fractional patient movements.

Apart from this, the method may be used both for rapid offline re-planning and also for initial irradiation planning for a patient.

The work that has led to this invention was supported in accordance with the financial aid agreement No. 215840 as part of the European Union's Seventh Framework Program (FP7/2007-2013).

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for producing an irradiation plan for a target volume by a computing device, the method comprising:
providing, by the computing device, a modulation curve that characterizes a modulation, in a direction of a beam, of particle numbers at target points that lie one behind another in the target volume;
determining, by the computing device, a current position of the target volume;
defining, by the computing device, a plurality of current target points that fully cover the target volume in the current position;
assigning, by the computing device, a selection of the particle numbers to the plurality of current target points using the modulation curve;
producing, by the computing device, the irradiation plan having the assigned particle numbers; and
irradiating the target volume using the irradiation plan.

2. The method as claimed in claim 1, further comprising determining, in a preliminary procedure, the modulation curve from at least one existing irradiation plan, in which the assigned particle numbers to the plurality of current target points in the target volume is stored.

3. The method as claimed in claim 2, wherein the target volume, used in the preliminary procedure for the determination of the modulation curve, belongs to a same person as the target volume, for which the current position is being determined, or wherein the target volume, used in the preliminary procedure for the determination of the modulation curve, belongs to a different person than does the target volume, for which the current position is being determined, or wherein the target volume, used in the preliminary procedure for the determination of the modulation curve, belongs to a phantom that simulates the target volume.

4. The method as claimed in claim 2, wherein determining, in the preliminary procedure, the modulation curve comprises averaging the particle numbers from a plurality of target point lines, wherein a target point line of the plurality of target point lines is defined by a number of the target points lying one behind another in the direction of the beam.

5. The method as claimed in claim 1, further comprising normalizing the modulation curve in terms of an energy level of the particle beam that is required for irradiation on the target volume.

6. The method as claimed in claim 1, wherein defining the plurality of current target points that fully cover the target volume comprises selecting a target point spacing that corresponds to a reference plan that already exists.

7. The method as claimed in claim 1, further comprising adapting, before the particle numbers are assigned to a target point line of the plurality of current target points, the particle numbers that are specified by the depth modulation curve in terms of an energy level that is required for the irradiation on the target volume, wherein the target point line is defined by a number of the target points lying one behind another in the direction of the beam.

8. The method as claimed in claim 1, further comprising using an existing irradiation plan, which has already been calculated with optimized physical or biological dose distribution, to produce the irradiation plan.

9. The method as claimed in claim 1, further comprising transferring an existing irradiation plan over to a new irradiation plan, wherein the existing irradiation plan and the new irradiation plan are assigned to a same patient, or wherein the existing irradiation plan and the new irradiation plan are assigned to different patients, or wherein the existing irradiation plan is assigned to a phantom, and the new irradiation plan is assigned to a patient.

10. The method as claimed in claim 1, further comprising determining first irradiation field particle numbers for a first irradiation field, wherein the depth modulation curve is determined from a second irradiation field that, by comparison with the first irradiation field, has a different angle of incidence.

11. The method as claimed in claim 1, further comprising:

providing additional depth modulation curves, the additional depth modulation curves and the depth modulation curve providing a plurality of depth modulation curves, wherein the plurality of depth modulation curves are produced from different irradiation plans that differ with respect to a target organ, a target dose, a type of particle to be used, a target point spacing, or a combination thereof; and selecting one depth modulation curve of the plurality of depth modulation curves in the assigning of the particle numbers to the plurality of current target points.

* * * * *